(12) United States Patent
Sheard et al.

(10) Patent No.: US 7,935,766 B2
(45) Date of Patent: May 3, 2011

(54) PROPYLENE IMPACT COPOLYMER AND METHOD

(75) Inventors: William G. Sheard, Missouri City, TX (US); Linfeng Chen, Sugar Land, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/650,625

(22) Filed: Dec. 31, 2009

(65) Prior Publication Data

US 2010/0168342 A1 Jul. 1, 2010

Related U.S. Application Data

(60) Provisional application No. 61/141,902, filed on Dec. 31, 2008, provisional application No. 61/141,959, filed on Dec. 31, 2008.

(51) Int. Cl.
*C08F 297/08* (2006.01)
*C08F 4/649* (2006.01)

(52) U.S. Cl. ...... 525/323; 525/247; 525/262; 526/124.9
(58) Field of Classification Search .................. 525/247, 525/262, 323; 526/124.9; 524/294
See application file for complete search history.

(56) References Cited

U.S. PATENT DOCUMENTS

| 4,882,380 | A | * | 11/1989 | Ficker et al. | 525/53 |
| 5,639,822 | A | * | 6/1997 | Hungenberg et al. | 525/53 |
| 7,141,635 | B2 | * | 11/2006 | Chen et al. | 526/128 |

FOREIGN PATENT DOCUMENTS

WO 03068828 8/2003

* cited by examiner

*Primary Examiner* — Fred M Teskin
(74) *Attorney, Agent, or Firm* — Whyte Hirschboeck Dudek SC

(57) ABSTRACT

Disclosed are propylene impact copolymer compositions, articles thereof, and processes for producing same. Polymerization with an improved catalyst composition provides a propylene impact copolymer with high melt flow and low volatiles content.

20 Claims, No Drawings

PROPYLENE IMPACT COPOLYMER AND METHOD

PRIORITY CLAIM

This application claims priority to U.S. provisional patent application Ser. No. 61/141,902 filed on Dec. 31, 2008, and U.S. provisional patent application Ser. No. 61/141,959 filed on Dec. 31, 2008, the entire content of each application incorporated by reference herein.

BACKGROUND

The demand for propylene impact copolymers with low volatile organic compound content continues to increase as the need for more sophisticated polymers continues to grow. The level of volatile organic compound or (VOC) content of a polymer determines how much VOC evaporates or vaporizes readily under normal or slightly elevated conditions. It is difficult to produce low-VOC-content propylene impact copolymers directly by polymerization. Conventional propylene impact copolymers typically undergo subsequent purge processes to lower the VOC content to acceptable levels.

Desirable is a polymerization process for the production of a propylene impact copolymer with improved properties and a low-VOC-content propylene impact copolymer in particular. Further desired is a process for the production of a low-VOC-content propylene impact copolymer that does not require subsequent purge processing to lower the VOC content.

SUMMARY

The present disclosure provides a process. In an embodiment, a process is provided and includes contacting, under polymerization conditions, propylene with a catalyst composition comprising a substituted phenylene aromatic diester in a first polymerization reactor. An active propylene-based polymer is formed in the first reactor. The process includes contacting, under polymerization conditions, the active propylene-based polymer with at least one olefin in a second reactor, and forming a propylene impact copolymer comprising a substituted phenylene aromatic diester.

In an embodiment, the process includes forming a propylene impact copolymer having a volatiles content less than about 30 μg/g as measured in accordance with VW standard PV3341.

The present disclosure provides a composition. In an embodiment, a propylene impact copolymer is provided and includes a propylene-based polymer, and a propylene/ethylene copolymer dispersed within the propylene-based polymer. The propylene impact copolymer also includes a substituted phenylene aromatic diester.

The present disclosure provides an article. In an embodiment, an article is provided and includes the foregoing propylene impact copolymer.

An advantage of the present disclosure is an improved propylene impact copolymer.

An advantage of the present disclosure is a propylene impact copolymer with high melt flow.

An advantage of the present disclosure is a propylene impact copolymer with low volatiles content.

An advantage of the present disclosure is a propylene impact copolymer that does not require a post-reactor purge process to lower volatiles content.

An advantage of the present disclosure is a propylene impact copolymer that is phthalate-free.

DETAILED DESCRIPTION

The present disclosure provides a process. In an embodiment, a polymerization process is provided and includes contacting, under polymerization conditions, propylene with a catalyst composition comprising a substituted phenylene aromatic diester in a first polymerization reactor. The process further includes forming an active propylene-based polymer. The process further includes contacting, under polymerization conditions, the active propylene-based polymer with at least one olefin in a second polymerization reactor, and forming a propylene impact copolymer comprising a substituted phenylene aromatic diester.

As used herein, "a catalyst composition" is a composition that forms an olefin-based polymer when contacted with an olefin under polymerization conditions. The catalyst composition includes a procatalyst composition, a cocatalyst, optionally an external electron donor, and optionally an activity limiting agent. The procatalyst composition includes a combination of a magnesium moiety, a titanium moiety and an internal electron donor. The internal electron donor includes the substituted phenylene aromatic diester.

The procatalyst composition is produced by halogenating/titanating a procatalyst precursor in the presence of the internal electron donor. As used herein, an "internal electron donor" is a compound added or otherwise formed during formation of the procatalyst composition that donates at least one pair of electrons to one or more metals present in the resultant procatalyst composition. The internal electron donor is the substituted phenylene aromatic diester. Not wishing to be bound by any particular theory, it is believed that during halogenation and titanation the internal electron donor (1) regulates the formation of active sites, (2) regulates the position of titanium on the magnesium-based support and thereby enhances catalyst stereoselectivity, (3) facilitates conversion of the magnesium and titanium moieties into respective halides and (4) regulates the crystallite size of the magnesium halide support during conversion. Thus, provision of the internal electron donor yields a procatalyst composition with enhanced stereoselectivity.

The procatalyst precursor may be a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The "MagMo precursor" contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carbonated magnesium dialkoxide or aryloxide. In one embodiment, the MagMo precursor is a magnesium di ($C_{1-4}$)alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3.

In an embodiment, the procatalyst precursor is a benzoate-containing magnesium chloride material. As used herein, a "benzoate-containing magnesium chloride" ("BenMag") is a magnesium chloride procatalyst (i.e., a halogenated procatalyst precursor) containing a benzoate internal electron donor. The BenMag material may also include a titanium moiety, such as a titanium halide. The benzoate internal donor is labile and can be replaced by other electron donors during procatalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Nonlimiting examples of suitable BenMag procatalyst precursors include catalysts of the trade names SHAC™ 103 and SHAC™ 310 available from The Dow Chemical Company, Midland, Mich.

In an embodiment, the BenMag procatalyst precursor is a product of halogenation of any procatalyst precursor (i.e., a MagMo precursor or a MagTi precursor) in the presence of a benzoate compound with the structure (I)

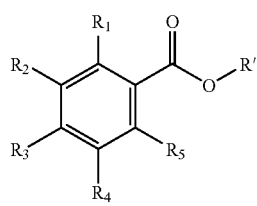

(I)

wherein $R_1$-$R_5$ are H, $C_1$-$C_{20}$ hydrocarbyl which may contain heteroatoms including F, Cl, Br, I, O, S, N, P, and Si, and R' is a $C_1$-$C_{20}$ hydrocarbyl group which may optionally contain heteroatom(s) including F, Cl, Br, I, O, S, N, P, and Si. Preferably, $R_1$-$R_5$ are selected from H and $C_1$-$C_{20}$ alkyl and R' is selected from $C_1$-$C_{20}$ alkyl and alkoxyalkyl.

Halogenation/titanation of the procatalyst precursor in the presence of the internal electron donor produces a procatalyst composition which includes a combination of a magnesium moiety, a titanium moiety, and the internal electron donor (a substituted phenylene aromatic diester). In an embodiment, the magnesium and titanium moieties are respective halides, such as magnesium chloride and titanium chloride. Bounded by no particular theory, it is believed that the magnesium halide is a support upon which the titanium halide is deposited and into which the internal electron donor is incorporated.

The resulting procatalyst composition has a titanium content of from about 1.0 percent by weight to about 6.0 percent by weight, based on the total solids weight, or from about 1.5 percent by weight to about 5.5 percent by weight, or from about 2.0 percent by weight to about 5.0 percent by weight. The weight ratio of titanium to magnesium in the solid procatalyst composition is suitably between about 1:3 and about 1:160, or between about 1:4 and about 1:50, or between about 1:6 and 1:30. The internal electron donor is present in an amount from about 0.1 wt % to about 20.0 wt %, or from about 1.0 wt % to about 15 wt %. The internal electron donor may be present in the procatalyst composition in a molar ratio of internal electron donor to magnesium of from about 0.005:1 to about 1:1, or from about 0.01:1 to about 0.4:1. Weight percent is based on the total weight of the procatalyst composition.

Ethoxide content in the procatalyst composition indicates the completeness of conversion of precursor metal ethoxide into a metal halide. The substituted phenylene aromatic diester assists in converting ethoxide into halide during halogenation. In an embodiment, the procatalyst composition includes from about 0.01 wt % to about 1.0 wt %, or from about 0.05 wt % to about 0.5 wt % ethoxide. Weight percent is based on the total weight of the procatalyst composition.

In an embodiment, the internal electron donor is a mixed internal electron donor. As used herein, a "mixed internal electron donor" is (i) a substituted phenylene aromatic diester, (ii) an electron donor component that donates a pair of electrons to one or more metals present in the resultant procatalyst composition, and (iii) optionally other components. In an embodiment, the electron donor component is a benzoate, such as ethyl benzoate and/or methoxypropan-2-yl benzoate. The procatalyst composition with the mixed internal electron donor can be produced by way of the procatalyst production procedure as previously disclosed.

The internal electron donor includes the substituted phenylene aromatic diester and optionally an electron donor component. The substituted phenylene aromatic diester may be a substituted 1,2-phenylene aromatic diester, a substituted 1,3 phenylene aromatic diester, or a substituted 1,4 phenylene aromatic diester. In an embodiment, the internal electron donor is a 1,2-phenylene aromatic diester with the structure (II) below:

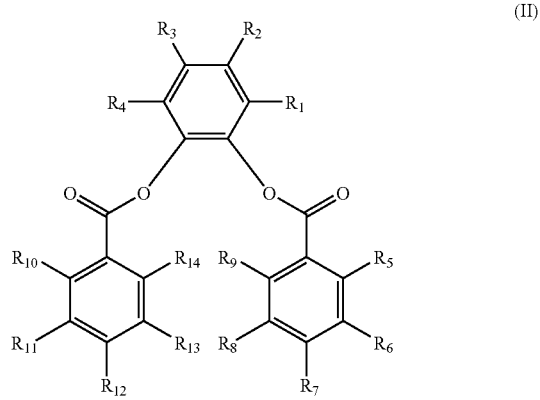

(II)

wherein $R_1$-$R_{14}$ are the same or different. Each of $R_1$-$R_{14}$ is selected from a hydrogen, substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. At least one of $R_1$-$R_{14}$ is not hydrogen.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F Cl, Br, I), N, O, P, B, S, and Si. A substituted hydrocarbyl group also includes a halohydrocarbyl group and a silicon-containing hydrocarbyl group. As used herein, the term "halohydrocarbyl" group refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

In an embodiment, at least one (or two, or three, or four) R group(s) of $R_1$-$R_4$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one (or some, or all) R group(s) of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_5$-$R_9$ and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one of $R_1$-$R_4$ and at least one of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_1$-$R_4$ at least one $R_5$-$R_9$ of and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, any consecutive R groups in $R_1$-$R_4$, and/or any consecutive R groups in $R_5$-$R_9$, and/or any consecutive R groups in $R_{10}$-$R_{14}$ may be linked to form an inter-cyclic or an intra-cyclic structure. The inter-/intra-cyclic structure may or may not be aromatic. In an embodiment, the inter-/intra-cyclic structure is a $C_5$ or a $C_6$ membered ring.

In an embodiment, at least one of $R_1$-$R_4$ is selected from a substituted hydrocarbyl group having 1 to 20 carbon atoms, an unsubstituted hydrocarbyl group having 1 to 20 carbon atoms, and combinations thereof. Optionally, at least one of $R_5$-$R_{14}$ may be a halogen atom or an alkoxy group having 1 to 20 carbon atoms. Optionally, $R_1$-$R_4$, and/or $R_5$-$R_9$, and/or $R_{10}$-$R_{14}$ may be linked to form an inter-cyclic structure or an intra-cyclic structure. The inter-cyclic structure and/or the intra-cyclic structure may or may not be aromatic.

In an embodiment, any consecutive R groups in $R_1$-$R_4$, and/or in $R_5$-$R_9$, and/or in $R_{10}$-$R_{14}$, may be members of a $C_5$-$C_6$-membered ring.

In an embodiment, structure (II) includes $R_1$, $R_3$ and $R_4$ as hydrogen. $R_2$ is selected from a substituted hydrocarbyl group having 1 to 20 carbon atoms, an unsubstituted hydrocarbyl group having 1 to 20 carbon atoms, and combinations thereof $R_5$-$R_{14}$ are the same or different and each of $R_5$-$R_{14}$ is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_2$ that is methyl, and each of $R_5$-$R_{14}$ is hydrogen.

In an embodiment, structure (II) includes $R_2$ that is ethyl, and each of $R_5$-$R_{14}$ is hydrogen.

In an embodiment, structure (II) includes $R_2$ that is t-butyl, and each of $R_5$-$R_{14}$ is hydrogen.

In an embodiment, structure (II) includes $R_2$ that is ethoxycarbonyl, and each of $R_5$-$R_{14}$ is hydrogen.

In an embodiment, structure (II) includes $R_2$, $R_3$ and $R_4$ each as hydrogen and $R_1$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ that is methyl, and each of $R_5$-$R_{14}$ is hydrogen.

In an embodiment, structure (II) includes $R_2$ and $R_4$ that are hydrogen and $R_1$ and $R_3$ are the same or different. Each of $R_1$ and $R_3$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ and $R_3$ that are the same or different. Each of $R_1$ and $R_3$ is selected from a $C_1$-$C_8$ alkyl group, a $C_3$-$C_6$ cycloalkyl group, or a substituted $C_3$-$C_6$ cycloalkyl group. $R_5$-$R_{14}$ are the same or different and each of $R_5$-$R_{14}$ is selected from hydrogen, a $C_1$-$C_8$ alkyl group, and a halogen. Nonlimiting examples of suitable $C_1$-$C_8$ alkyl groups include methyl, ethyl, n-propyl, isopropyl, n-butyl, i-butyl, t-butyl, n-pentyl, i-pentyl, neopentyl, t-pentyl, n-hexyl, and 2,4,4-trimethylpentan-2-yl group. Nonlimiting examples of suitable $C_3$-$C_6$ cycloalkyl groups include cyclopentyl and cyclohexyl groups. In a further embodiment, at least one of $R_5$-$R_{14}$ is a $C_1$-$C_6$ alkyl group or a halogen.

In an embodiment, structure (II) includes $R_1$ that is a methyl group and $R_3$ that is a t-butyl group. Each of $R_2$, $R_4$ and $R_5$-$R_{14}$ is hydrogen.

In an embodiment, structure (II) includes $R_1$ and $R_3$ that is an isopropyl group. Each of $R_2$, $R_4$ and $R_5$-$R_{14}$ is hydrogen.

In an embodiment, structure (II) includes each of $R_1$, $R_5$, and $R_{10}$ as a methyl group and $R_3$ is a t-butyl group. Each of $R_2$, $R_4$, $R_6$-$R_9$ and $R_{11}$-$R_{14}$ is hydrogen.

In an embodiment, structure (II) includes each of $R_1$, $R_7$, and $R_{12}$ as a methyl group and $R_3$ is a t-butyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ as a methyl group and $R_3$ is a t-butyl group. Each of $R_7$ and $R_{12}$ is an ethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes each of $R_1$, $R_5$, $R_7$, $R_9$, $R_{10}$, $R_{12}$, and $R_{14}$ as a methyl group and $R_3$ is a t-butyl group. Each of $R_2$, $R_4$, $R_6$, $R_8$, $R_{11}$, and $R_{13}$ is hydrogen.

In an embodiment, structure (II) includes $R_1$ as a methyl group and $R_3$ is a t-butyl group. Each of $R_5$, $R_7$, $R_9$, $R_{10}$, $R_{12}$, and $R_{14}$ is an i-propyl group. Each of $R_2$, $R_4$, $R_6$, $R_8$, $R_{11}$, and $R_{13}$ is hydrogen.

In an embodiment, the substituted phenylene aromatic diester has a structure (III) which includes $R_1$ that is a methyl group and $R_3$ is a t-butyl group. Each of $R_2$ and $R_4$ is hydrogen. $R_8$ and $R_9$ are members of a $C_6$ membered ring to form a 1-naphthoyl moiety. $R_{13}$ and $R_{14}$ are members of a $C_6$ membered ring to form another 1-naphthoyl moiety. Structure (III) is provided below.

(III)

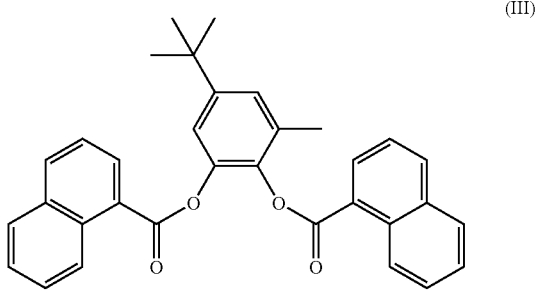

In an embodiment, the substituted phenylene aromatic diester has a structure (IV) which includes $R_1$ that is a methyl group and $R_3$ is a t-butyl group. Each of $R_2$ and $R_4$ is hydrogen. $R_6$ and $R_7$ are members of a $C_6$ membered ring to form a 2-naphthoyl moiety. $R_{12}$ and $R_{13}$ are members of a $C_6$ membered ring to form a 2-naphthoyl moiety. Structure (IV) is provided below.

(IV)

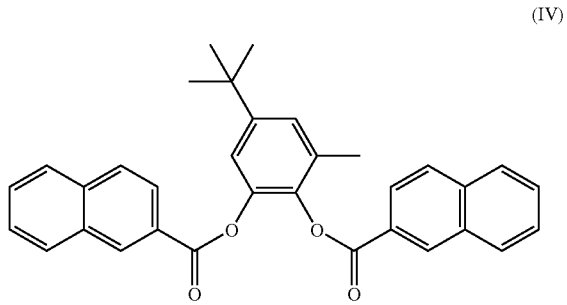

In an embodiment, structure (II) includes $R_1$ that is a methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a fluorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a chlorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a bromine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an iodine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_6$, $R_7$, $R_{11}$, and $R_{12}$ is a chlorine atom. Each of $R_2$, $R_4$, $R_5$, $R_8$, $R_9$, $R_{10}$, $R_{13}$, and $R_{14}$ is hydrogen.

In an embodiment, structure (II) includes $R_1$ that is a methyl group and $R_3$ is a t-butyl group. Each of $R_6$, $R_8$, $R_{11}$, and $R_{13}$ is a chlorine atom. Each of $R_2$, $R_4$, $R_5$, $R_7$, $R_9$, $R_{10}$, $R_{12}$, and $R_{14}$ is hydrogen.

In an embodiment, structure (II) includes $R_1$ that is a methyl group and $R_3$ is a t-butyl group. Each of $R_2$, $R_4$ and $R_5$-$R_{14}$ is a fluorine atom.

In an embodiment, structure (II) includes $R_1$ that is a methyl group and $R_3$ is a t-butyl group. Each of $R_7$ and $R_{12}$ is a trifluoromethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an ethoxycarbonyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, $R_1$ is a methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a diethylamino group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a 2,4,4-trimethylpentan-2-yl group. Each of $R_2$, $R_4$ and $R_5$-$R_{14}$ is hydrogen.

In an embodiment, structure (II) includes $R_1$ and $R_3$, each of which is a sec-butyl group. Each of $R_2$, $R_4$ and $R_5$-$R_{14}$ is hydrogen.

In an embodiment, the substituted phenylene aromatic diester has a structure (V) whereby $R_1$ and $R_2$ are members of a $C_6$ membered ring to form a 1,2-naphthalene moiety. Each of $R_5$-$R_{14}$ is hydrogen. Structure (V) is provided below.

(V)

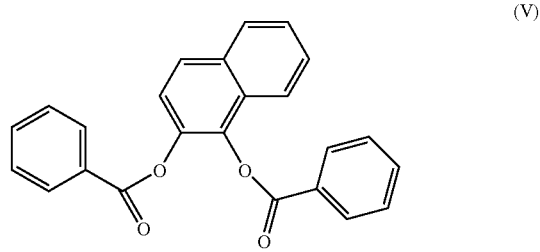

In an embodiment, the substituted phenylene aromatic diester has a structure (VI) whereby $R_2$ and $R_3$ are members of a $C_6$ membered ring to form a 2,3-naphthalene moiety. Each of $R_5$-$R_{14}$ is hydrogen. Structure (VI) is provided below.

(VI)

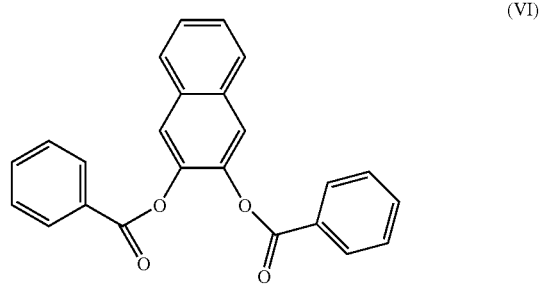

In an embodiment, structure (II) includes $R_1$ and $R_4$ that are each a methyl group. Each of $R_2$, $R_3$, $R_5$-$R_9$ and $R_{10}$-$R_{14}$ is hydrogen.

In an embodiment, structure (II) includes $R_1$ that is a methyl group. $R_4$ is an i-propyl group. Each of $R_2$, $R_3$, $R_5$-$R_9$ and $R_{10}$-$R_{14}$ is hydrogen.

In an embodiment, structure (II) includes $R_1$, $R_3$, and $R_4$, each of which is an i-propyl group. Each of $R_2$, $R_5$-$R_9$ and $R_{10}$-$R_{14}$ is hydrogen.

The catalyst composition includes a cocatalyst. As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum compound represented by the formula $R_nAlX_{3-n}$ wherein n=1 2, or 3, R is an alkyl, and X is a halide or alkoxide. Nonlimiting examples of suitable cocatalyst include from trimethylaluminum, triethylaluminum, triisobutylaluminum, and tri-n-hexylaluminum.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1, or from about 30:1 to about 60:1. In another embodiment, the molar ratio of aluminum to titanium is about 35:1.

In an embodiment, the present catalyst composition includes an external electron donor. As used herein, an "external electron donor" (or "EED") is a compound added independent of procatalyst formation and includes at least one functional group that is capable of donating a pair of electrons to a metal atom. A "mixed external electron donor" (or "MEED") is a mixture of two or more external electron donors. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the external electron donor may be selected from one or more of the following: a silicon compound, a bidentate compound, an amine, an ether, a carboxylate, a ketone, an amide, a carbamate, a phosphine, a phosphate, a phosphite, a sulfonate, a sulfone, a sulfoxide, and any combination of the foregoing.

In an embodiment, the EED is a silicon compound having the general formula (VII):

$$SiR_m(OR')_{4-m} \quad\quad (VII)$$

wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, or 2. In an embodiment, R is $C_{6-12}$ aryl, alkylaryl or aralkyl, $C_{3-12}$ cycloallyl, $C_{1-20}$ linear alkyl or alkenyl, $C_{3-12}$ branched alkyl, or $C_{3-12}$ cyclic amino group, R' is $C_{1-4}$ alkyl, and m is 1 or 2.

Nonlimiting examples of suitable silicon compounds for the EED include dialkoxysilanes, trialkoxysilanes, and tetraalkoxysilanes such as dicyclopentyldimethoxysilane (DCPDMS), diisopropyldimethoxysilane, bis(perhydroisoquinolino)dimethoxysilane, methylcyclohexyldimethoxysilane, tetraethoxysilane, n-propyltrimethoxysilane, n-propyltriethoxysilane, diethylaminotriethoxysilane, bis(trimethylsilylmethyl)dimethoxysilane, and any combination thereof.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the softening point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The ALA may or may not be a component of the EED and/or the MEED. The activity limiting agent may be a carboxylic acid ester, a diether, a poly(alkene glycol), a succinate, a diol ester, and combinations thereof. The carboxylic acid ester can be an aliphatic or aromatic, mono- or polycarboxylic acid ester. Nonlimiting examples of suitable carboxylic acid esters include benzoates, $C_{1-40}$ alkyl esters of aliphatic $C_{2-40}$ mono-/di-carboxylic acids, $C_{2-40}$ mono-/polycarboxylate derivatives of $C_{2-100}$ (poly)glycols, $C_{2-100}$ (poly)glycol ethers, and any combination thereof. Further nonlimiting examples of carboxylic acid esters include laurates, myristates, palmitates, stearates, oleates, sebacates, and (poly)(alkylene)glycols, and mixtures thereof. In a further embodiment, the ALA is isopropyl myristate or di-n-butyl sebacate.

The catalyst composition may include any of the foregoing external electron donors in combination with any of the foregoing activity limiting agents. The external electron donor and/or activity limiting agent can be added into the reactor separately. Alternatively, the external electron donor and the activity limiting agent can be mixed together in advance and then added to the catalyst composition and/or into the reactor as a mixture.

The process includes contacting, under polymerization conditions, propylene with the catalyst composition containing the substituted phenylene aromatic diester in a first polymerization reactor to form an active propylene-based polymer. As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, reactor.

It is understood that provision of hydrogen in the polymerization reactor is a component of the polymerization conditions. During polymerization, hydrogen is a chain transfer agent and affects the molecular weight (and correspondingly the melt flow rate) of the resultant polymer. The polymerization process may include a pre-polymerization step and/or a pre-activation step.

One or more olefin comonomers can be introduced into the first polymerization reactor along with the propylene to react with the catalyst and to form a polymer, or a fluidized bed of polymer particles. Nonlimiting examples of suitable olefin monomers include ethylene (for purposes of this disclosure, ethylene is considered an α-olefin), $C_{4-20}$ α-olefins, such as 1-butene, 1-pentene, 1-hexene, 4-methyl-1-pentene, 1-heptene, 1-octene, 1-decene, 1-dodecene and the like. In an embodiment, propylene is introduced into the first polymerization reactor to form a propylene homopolymer.

In an embodiment, the process includes maintaining an Al:EED molar ratio of less than 5.0, or from 2.0 to less than 5.0, in the first polymerization reactor. Bounded by no particular theory, it is believed that an Al:EED molar ratio of less than 5.0 (in conjunction with the presence of the substituted phenylene aromatic diester) contributes to the formation of a propylene-based polymer with high stiffness and high melt flow by enhancing or otherwise improving the crystallinity of the formant propylene-based polymer.

In an embodiment, the process includes adding a single EED to the first polymerization reactor. The single EED is DCPDMS.

The present process advantageously produces a propylene-based polymer with high stiffness and high melt flow without visbreaking—a conventional technique for increasing the MFR beyond the hydrogen usage limitations of a reactor-grade high stiffness propylene-based polymer as described previously. The term "visbreaking" (or "cracking"), as used herein, is the thermal and/or chemical degradation of a polymer into smaller polymer chain segments. Visbreaking typically includes placing a polymer (such as polypropylene) in a melt state in the presence of a free radical initiator (such as a peroxide) to degrade the polypropylene into smaller polypropylene chain segments. Visbreaking is a post-reactor procedure. It is understood that the present processes for producing propylene impact copolymer are in-reactor, polymerization processes. Thus the present processes for producing propylene impact copolymer do not include visbreaking.

Visbreaking has many side effects such as formation of decomposition products (which oftentimes cause odor and food incompatibility problems), added cost, and a reduction in polymer stiffness. Visbreaking increases the melt flow yet decreases the weight average molecular weight of a polymer. Visbreaking alters the physical and chemical structure of the initial polymer. For example, a visbroken polypropylene homopolymer will exhibit a reduction in physical and/or mechanical properties (i.e., a lower tensile modulus, a lower flexural modulus) compared to an uncracked propylene homopolymer with the same MFR.

In an embodiment, the present process forms an uncracked propylene-based polymer. A polymer that is "uncracked" has not been subject to a visbreaking procedure. In other words, an uncracked polymer is a non-thermally and/or non-chemically degraded polymer. An uncracked polymer does not exhibit a decline of physical and/or mechanical properties related to molecular weight (such as flexural modulus and/or tensile properties), as does a visbroken polymer at the same MFR. In addition, an uncracked polymer does not experience decomposition products (which oftentimes cause odor and food incompatibility problems) as does a visbroken polymer.

In an embodiment, the process includes forming a propylene-based polymer having one or more of the following properties: (i) an uncracked propylene homopolymer; (ii) a MFR greater than 100 g/10 min, or from 100 g/10 min to 200 g/10 min; (iii) a xylene solubles content of less than 3% wt %, or from about 0.1 wt % to less than 2.0 wt %; and/or (iv) a $T_{MF}$ greater than about 165° C., or greater than 170° C.

In an embodiment, the uncracked propylene-based polymer is a propylene homopolymer. In a further embodiment, the propylene-based polymer has low or no toxicity, low or no decomposition products, and low or no unpleasant odor. The propylene-based polymer is phthalate-free.

The active propylene-based polymer is introduced into a second polymerization reactor and contacted, under polymerization conditions, with at least one olefin in a second reactor to form a propylene impact copolymer. The formed propylene impact copolymer includes the substituted phenylene aromatic diester (i.e., the internal electron donor of the catalyst composition). As used herein, an "active propylene-based polymer" is a polymer containing an amount of active catalyst (typically embedded therein) that is capable of further polymerization upon exposure to an olefin under polymerization conditions. The active propylene-based polymer is the product of a previous polymerization process performed in the first reactor. The active propylene-based polymer may or may not be produced in the presence of an SCA and/or an ALA. In another embodiment, the first polymerization reactor and the second polymerization reactor operate in series (i.e., linked gas phase reactors), whereby the effluent from the first polymerization reactor is charged to the second polymerization reactor and one or more additional (or different) olefin monomer(s) is/are added to the second polymerization reactor to continue polymerization.

In an embodiment, the process includes forming a propylene impact copolymer having a volatiles content less than about 30 μg/g, or from about 5 μg/g to about 30 μg/g, or from about 10 μg/g to about 27 μg/g in accordance with VW standard PV3341. Not bounded by any particular theory, it is believed that the presence of the substituted phenylene aromatic diester (alone or in combination with the $H_2/C_3$ ratio) contributes to the low level of volatiles content of the resultant propylene impact copolymer. As used herein, "volatiles" are carbon-containing substances that are driven off as vapor at room temperature or slightly elevated temperatures, from a polymer. A nonlimiting example of volatiles are low molecular weight oligomers formed during polymerization.

In an embodiment, the internal electron donor is a substituted phenylene aromatic diester. Consequently, the substituted phenylene aromatic diester is present in the propylene-based polymer, the propylene/ethylene copolymer, and combinations thereof.

The low amount of volatiles content of the present propylene impact copolymer advantageously reduces, or eliminates, a subsequent purge procedure. Conventional propylene impact copolymers typically require a nitrogen purge and/or a steam purge (for several days) in order to reduce the volatiles content to acceptable levels—particularly for applications requiring low volatiles content, such as food container applications. The low volatiles content of the present propylene impact copolymer decreases purge time or eliminates a purge procedure altogether.

In an embodiment, the polymerization process includes maintaining a hydrogen-to-propylene ("$H_2/C_3$") mole ratio greater than 0.1, or from 0.1 to 0.3, or from 0.2 to 0.3, in the second polymerization reactor. Applicants have surprisingly discovered that polymerization at this $H_2/C_3$ mole ratio in conjunction with the presence of the substituted phenylene aromatic diester unexpectedly contributes to the low volatiles content in the final propylene impact copolymer.

An unwanted side effect of increasing the $H_2/C_3$ molar ratio during Ziegler-Natta polymerization is a corresponding increase in the production of low molecular weight oligomers. These low molecular weight oligomers are volatile and contribute to a high volatiles content in the formant polymer. Surprisingly, provision of the substituted phenylene aromatic diester in the present catalyst composition unexpectedly maintains an exceptionally low volatiles content (i.e., less than 30 μg/g volatiles content) in the formant polymer as $H_2/C_3$ molar ratio increases. Stated differently, the present catalyst composition with the substituted phenylene aromatic diester enables the production of polymer having low volatiles content at high $H_2/C_3$ molar ratio during polymerization.

In an embodiment, the process includes contacting the active propylene-based polymer with propylene and ethylene in the second polymerization reactor under polymerization conditions, and forming a propylene impact copolymer having a melt flow rate greater than about 40 g/10 min, or greater than about 60 g/10 min, or greater than about 80 g/10 min, or from greater than 40 g/10 min to about 100 g/10 min as measured in accordance with ASTM D1238, 2.16 kg, 230° C.

In an embodiment, the propylene impact copolymer has an Fc value from about 5 wt % to about 50 wt %, or from about 10 wt % to about 40 wt %, or from about 15 wt % to about 25 wt %. As used herein, "fraction copolymer" ("Fc") is the weight percent of the discontinuous phase present in the heterophasic copolymer. The Fc value is based on the total weight of the propylene impact copolymer.

In an embodiment, the propylene impact copolymer has an Ec value from about 20% wt to about 90 wt %, or from about 30 wt % to about 80 wt %, or from about 40 wt % about 60 wt %. As used herein, "ethylene content" ("Ec") is the weight percent of ethylene present in the discontinuous phase of the propylene impact copolymer. The Ec value is based on the total weight of the discontinuous (or rubber) phase.

In an embodiment, the process includes melt blending a nucleating agent with the propylene impact copolymer and forming a nucleated propylene impact copolymer. As used herein, "melt blending" is a process in which a polymer is softened and/or melted and mixed with one or more other compounds. Nonlimiting examples of melt blending processes include extrusion, melt mixing (batch or continuous), reactive melt blending, and/or compounding.

The nucleating agent increases the crystallinity of the polymer, and thereby increases the stiffness of the propylene impact copolymer. Not wishing to be bound by any particular theory, it is believed that the nucleating agent provides sites for more ordered and faster polyolefin crystallization during cooling. During the process of crystallization, polymer crystals organize into larger superstructures which are referred to as spherulites. The spherulites are more uniform and are smaller in size than spherulites formed in the absence of the nucleating agent.

Various nucleating agents known in the art may be used without limitation. Nonlimiting examples of suitable nucleating agents include sodium benzoate, aluminum adipate; aluminum p-t-butylbenzoate; sorbitol acetal derivatives such as 1,3,2,4-dibenzylidenesorbitol, 1,3,2,4-bis(p-methyl-benzylidene)sorbitol, 1,3,2,4-bis(p-ethylbenzylidene)-sorbitol, 1,3-p-chlorobenzylidene-2,4-p-methylbenzylidene-sorbitol, 1,3-O-2,4-bis(3,4-dimethylbenzylidene)sorbitol, (available from Milliken Chemical Spartanburg, S.C. under the trade name Millad® 3988), 1,3-O-2,4-bis(p-methylbenzylidene) sorbitol (also available from Milliken Chemical under the trade name Millad® 3940); sodium bis(4-t-butylphenyl) phosphate; sodium bis(4-t-methylphenyl) phosphate; potassium bis(4,6-di-t-butylphenyl) phosphate; sodium 2,2'-methylene-bis(4,6-di-t-butylphenyl) phosphate (NA-11); sodium 2,2'-ethylidene-bis(4,6-di-t-butylphenyl) phosphate; talc; calcium carbonate; and any combination of the foregoing.

The process may comprise two or more embodiments disclosed herein.

The present disclosure provides a propylene impact copolymer. In an embodiment, a propylene impact copolymer is provided and includes a propylene-based polymer (matrix or continuous phase) with a propylene/ethylene copolymer (discontinuous phase) dispersed therein. The propylene impact copolymer also includes a substituted phenylene aromatic diester.

The substituted phenylene aromatic diester is present in the propylene-based polymer, the propylene/ethylene copolymer, and combinations thereof. In an embodiment, the substituted phenylene aromatic diester is 3-methyl-5-tert-butyl-1,2 phenylene dibenzoate.

In an embodiment, propylene-based polymer has a MFR greater than about 100 g/10 min, or greater than 140 g/10 min, or from about 100 g/10 min to about 250 g/10 min. The propylene impact copolymer has a melt flow rate greater than about 40 g/10 min to about 100 g/10 min as previously disclosed, an Fc value from about 5 wt % to about 50 wt %, an Ec value from about 20 wt % to about 90 wt %.

In an embodiment, the propylene-based polymer has a MFR greater than about 140 g/10 min and the propylene impact copolymer has a MFR greater than about 80 g/10 min. In a further embodiment, the propylene-based polymer is a propylene homopolymer.

In an embodiment, the propylene-based polymer has one or more of the following properties: xylene solubles content of less than about 4 wt %, or less than about 2 wt %; and a $T_{MF}$ greater than about 170° C.

In an embodiment, no polymer component of the propylene impact copolymer is cracked or otherwise visbroken. In other words, the propylene impact copolymer is uncracked, the propylene-based polymer is uncracked, and the propylene/ethylene copolymer is uncracked.

In an embodiment, the propylene impact copolymer has a volatiles content of less than about 30 μg/g, or from 5 μg/g to about 30 μg/, or from 10 μg/g to about 27 μg/as measured in accordance with VW standard PV3341.

In an embodiment, the propylene impact copolymer is a nucleated propylene impact copolymer.

The present disclosure provides an article. In an embodiment, an article is provided and includes a propylene impact copolymer. The propylene impact copolymer may be any propylene impact copolymer that contains a substituted phenylene aromatic diester as disclosed herein.

In an embodiment, the article is a molded article. The molded article may be an extruded article, an injection molded article, a blow molded article, a rotation molded article, and a thermoformed article.

The present propylene impact copolymer may be used for a variety of applications such as automotive interior parts where low volatiles are required, and can be used for many food contact applications such as cups and containers. Additionally, many ordinary molded articles such as toys, pails, buckets, and general purpose articles can take advantage of the high melt flow product and impact strength properties and/or low volatiles content of the present propylene impact copolymer. The present propylene impact copolymer can also be used to produce fibers for carpets, upholstery, and diapers.

In an embodiment, the catalyst composition, the propylene impact copolymer produced therefrom, and/or articles composed of the propylene impact copolymer is/are phthalate-free, or is/are otherwise void or devoid of phthalate and/or phthalate derivatives.

The propylene impact copolymer and articles composed thereof may comprise two or more embodiments disclosed herein.

DEFINITIONS

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

Test Methods

The final melting point (Tmf) is the temperature to melt the most perfect crystal and is regarded as a measure of polymer crystallinity. It is measured on a TA Q100 differential scanning calorimeter. A sample is heated from 0° C. to 240° C. at a rate of 80° C./min, cooled at the same rate to 0° C., then heated again at the same rate up to 150° C., held at 150° C. for 5 minutes and the heated from 150° C. to 180° C. at 1.25° C./min. The Tm(f) is determined from this last cycle by calculating the onset of the baseline at the end of the heating curve.

Flexural modulus (1% SFM) is determined in accordance with ASTM D790-00 Method I, using an ASTM D 638 Type 1 injection molded specimen tested at 1.3 mm/min.

ISO flex chord modulus is determined in accordance with ISO 527, tested at 1.3 mm/min.

ASTM Izod impact is determined in accordance with ASTM D 256A.

ISO Izod impact is determined in accordance with ISO 180.

Gardner Impact is determined in accordance with ASTM D5420, method GC, using a 3.2 mm thick disk. Testing is done at −30° C.

Melt flow rate (MFR) is measured in accordance with ASTM D 1238-01 test method at 230° with a 2.16 kg weight for propylene-based polymers.

Volatiles content—is measured by the static Headspace Analysis described in the textbook: Pyrolysis and GC in Polymer Analysis, edited by S. A. Liebman and E. J. Levy, Marcel Dekker, Inc., 1985. The gas chromatography/headspace gas chromatography (GC-HS) analysis is widely used in the automotive industry. The company Volkswagen AG has developed a standard, which is generally accepted and used in the plastic industry. It is known as "VW standard PV 3341" (or "PV3341"). PV 3341 is a test in which a sample of 2 grams is placed into a headspace vial, conditioned for 5 hours at 120° C. and then injected into a GC. Quantification is accomplished using an external standard technique based on peak area response of acetone standards.

Xylene Solubles (XS) is measured according to the following procedure. 0.4 g of polymer is dissolved in 20 ml of xylenes with stirring at 130° C. for 30 minutes. The solution is then cooled to 25° C. and after 30 minutes the insoluble polymer fraction is filtered off. The resulting filtrate is analyzed by Flow Injection Polymer Analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration was maintained with Viscotek PolyCAL™ polystyrene standards.

By way of example and not by limitation, examples of the present disclosure will now be provided.

EXAMPLES

1. Substituted Phenylene Aromatic Diester

Substituted phenylene aromatic diester may be synthesized in accordance with provisional U.S. patent application Ser. No. 61/141,959 filed on Dec. 31, 2008, the entire content of which is incorporated by reference herein. Nonlimiting examples of suitable substituted phenylene aromatic diester are provided in Table 1 below.

TABLE 1

| Compound | Structure | $^1$H NMR (500 MHz, CDCl$_3$, ppm) |
|---|---|---|
| 3-methyl-5-tert-butyl-1,2-phenylene dibenzoate | 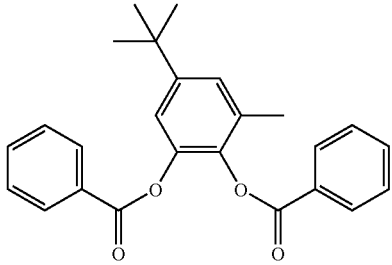 | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | 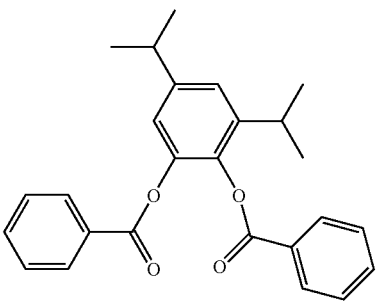 | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 3,6-dimethyl-1,2-phenylene dibenzoate | 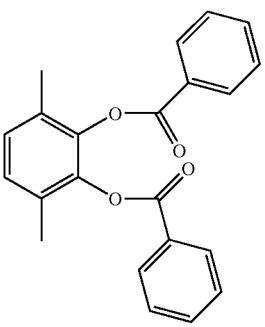 | δ 8.08 (d, 2H), 7.51 (t, 1H), 7.34 (d, 2H), 7.11 (s, 2H), 2.23 (s, 6H). |
| 4-t-butyl-1,2-phenylene dibenzoate | 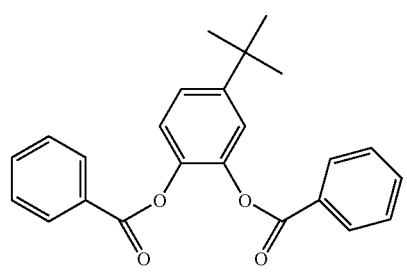 | δ 8.07 (dd, 4H), 7.54 (m, 2H), 7.30-7.40 (m, 7H), 1.37 (s, 9H). |

TABLE 1-continued

| Compound | Structure | $^1$H NMR (500 MHz, CDCl$_3$, ppm) |
|---|---|---|
| 4-methyl 1,2-phenylene dibenzoate | 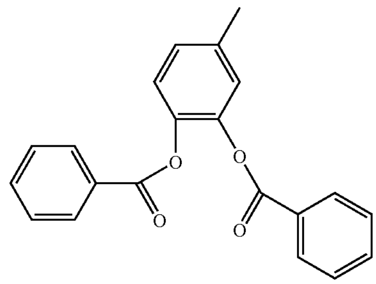 | δ (ppm) 8.07 (d, 4H), 7.54 (t, 2H), 7.37 (t, 4H), 7.27 (d, 1H), 7.21 (s, 1H), 7.15 (d, 1H), 2.42 (s, 3H). |
| 1,2-naphthalene dibenzoate | 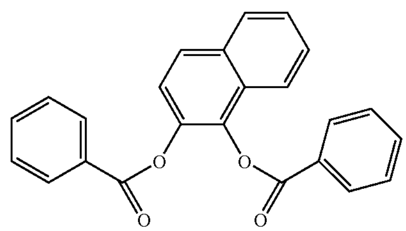 | δ 8.21-8.24 (m, 2H), 8.08-8.12 (m, 2H), 7.90-7.96 (m, 2H), 7.86 (d, 1H), 7.60 (m, 1H), 7.50-7.55 (m, 4H), 7.46 (t, 2H), 7.37 (t, 2H). |
| 2,3-naphthalene dibenzoate | 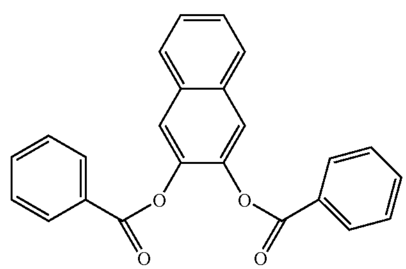 | δ 8.08-8.12 (m, 4H), 7.86-7.90 (m, 4H), 7.51-7.58 (m, 4H), 7.38 (t, 4H) |
| 3-methyl-5-tert-butyl-1,2-phenylene di(4-methylbenzoate) | 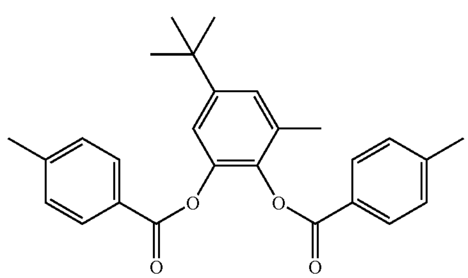 | δ (ppm) 7.98 (d, 2H), 7.93 (d, 2H), 7.18 (d, 4H), 7.15 (d, 2H), 2.38 (s, 3H), 2.36 (s, 3H), 2.26 (s, 3H), 1.35 (s, 9H). |
| 3-methyl-5-tert-butyl-1,2-phenylene di(2,4,6-trimethylbenzoate) | 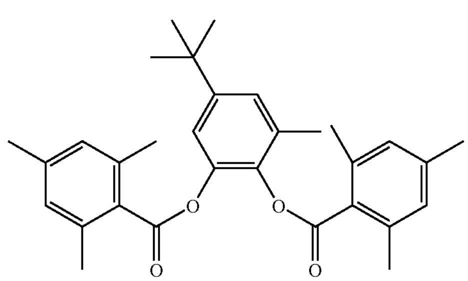 | δ (ppm) 7.25 (s, 1H), 7.21 (s, 1H), 6.81 (d, 4H), 2.36 (s, 3H), 2.30 (d, 6H), 2.25 (s, 6H), 2.23 (s, 6H), 1.36 (s, 9H). |

TABLE 1-continued

| Compound | Structure | $^1$H NMR (500 MHz, CDCl$_3$, ppm) |
|---|---|---|
| 3-methyl-5-tert-butyl-1,2-phenylene di(4-fluorobenzoate) | 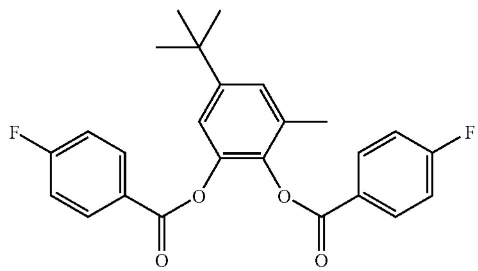 | δ 7.98 (dd, 4H), 7.36 (dd, 4H), 7.21 (s, 1H), 7.17 (s, 1H), 2.26 (s, 3H), 1.34 (s, 9H). |
| 3-methyl-5-tert-butyl-1,2-phenylene di(4-chlorobenzoate) | 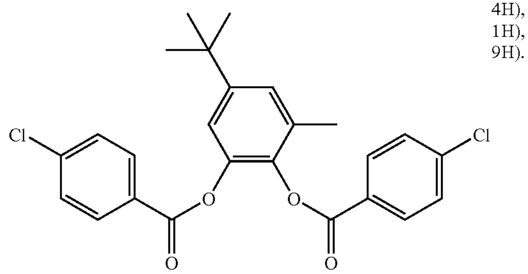 | δ 7.98 (dd, 4H), 7.36 (dd, 4H), 7.21 (s, 1H), 7.17 (s, 1H), 2.26 (s, 3H), 1.34 (s, 9H). |

2. Procatalyst Compositions

Catalyst 1 At ambient temperature, 351 g of a mixed magnesium/titanium halide alcoholate is agitated in a mixture of 1.69 kg of chlorobenzene and 4.88 kg of titanium(IV) chloride. After 10 minutes, 750 mL of a chlorobenzene solution containing 164.5 g of 5-tert-butyl-3-methyl-1,2-phenylene dibenzoate is added, followed by an additional 0.46 kg of chlorobenzene. The mixture is agitated at 100° C. for 60 minutes, allowed to settle, then filtered at 100° C. The solids are agitated in 3.16 kg of chlorobenzene at 70° C. for 15 minutes, allowed to settle, then filtered at 70° C. The solids are agitated in a mixture of 2.36 kg of chlorobenzene and 4.84 kg of titanium(IV) chloride, and after 10 minutes, a solution of 109.7 g of 5-tert-butyl-3-methyl-1,2-phenylene dibenzoate in 416 g of chlorobenzene is added, followed by an additional 0.20 kg of chlorobenzene. The mixture is agitated at 105-110° C. for 30 minutes, allowed to settle, then filtered at 105-110° C. The solids are agitated in a mixture of 3.10 kg of chlorobenzene and 4.84 kg of titanium(IV) chloride at 105-110° C. for 30 minutes, allowed to settle, then filtered at 105-110° C. After cooling, the solids are washed twice with 3.47 kg of hexane at 45° C., followed by a final wash with 3.47 kg of 2-methylbutane at ambient temperature. The solids are subjected to vacuum to remove residual volatiles, then combined with 683 g of mineral to generate a slurry.

Comparative Sample 1 (CS1) is SHAC™ 320, a magnesium-titanium containing catalyst (MagTi) with di-isobutyl phthalate as internal electron donor.

Comparative Sample 2 (CS2) is procatalyst FV, a Ziegler-Natta procatalyst composition with a 1,3-diether internal electron donor as disclosed in European Patent Application No. 728,769. The FV procatalyst is prepared as follows.

At ambient temperature, 350 g of a mixed magnesium/titanium halide alcoholate, 72 g of 9,9-bis(methoxymethyl)-9H-fluorene, and 5.6 L of a 50/50 (vol/vol) mixture of titanium(IV) chloride and chlorobenzene are combined. The mixture is agitated at 105-115° C. for 60 min, allow to settle, and filtered at 100° C. The solids are agitated in 2.8 L of chlorobenzene at 85° C., allowed to settle, and filtered at 85° C. The solids are twice stirred in 5.6 L of a fresh mixture of 50/50 titanium(IV) chloride and chlorobenzene at 105-115° C. for 30 min, is allowed to settle, and is filtered at 100° C. After cooling, the solids are washed twice with 5.2 L of hexane at 50-60° C., followed by a final wash with 5.6 L of 2-methylbutane at ambient temperature. The solids are combined with 1.19 kg of mineral oil, and the resulting slurry was subjected to vacuum to remove residual volatiles.

3. Polymerization

Production of the samples A-G is performed in the gas phase using linked fluidized bed reactors such as described in U.S. Pat. No. 4,882,380, the entire content of which is incorporated by reference herein. Polymerization conditions are those listed in Table 2 below.

As a final step in the production of samples A-F, each sample is semi-continuously discharged into a fiberpak and sparged (or deactivated) with wet nitrogen at 22° C., using approximately 3 kg of water per 1000 kg of resin for a period up to 3 hours.

After resin from sample G is discharged from the reactor, it is deactivated by purging for 1-3 hours with wet nitrogen at 22° C., using 1 kg of water per 1000 kg of polymer.

Samples A-G are nucleated as shown in Table 3 below.

TABLE 2

|  | A | B | C | D* | E* | F* | G* |
|---|---|---|---|---|---|---|---|
| Rx 1 Conditions | | | | | | | |
| Catalyst | 1 | 1 | 1 | CS1 | CS1 | CS2 | CS1 |
| Rx 1 $H_2/C_3$ | 0.148 | 0.148 | 0.147 | 0.144 | 0.15 | 0.075 | 0.178 |
| Rx Temp (C.) | 70 | 70 | 70 | 70 | 70 | 70 | 65 |
| Molar Al/DCPDMS | 4.6 | 4.5 | 4.5 | 21.0 | 13.3 | 4.3 | 1 |
| Molar Al/TEOS | na | na | Na | | 8.0 | na | na |
| Molar/Al/PTES | na | na | Na | 7.0 | na | na | na |
| Molar/Al/IPM | na | na | Na | 3.5 | 3.3 | 2.8 | na |
| Rx 1 Al/SCA | na | na | Na | 2.1 | 2 | 1.7 | na |
| Rx 1 Al/Ti | 49 | 50 | 50 | 49 | 49 | 49 | 40 |
| Propylene partial pressure (kPa) | 1930 | 1933 | 1940 | 2215 | 2208 | 2202 | 2622 |
| Rx 1 residence time (hours) | 2.3 | 2.3 | 5.3 | 2.7 | 2.9 | 3.3 | 1.3 |
| MFR(g/10 min) (homopolymer) | 145 | 146 | 178 | 139.0 | 153.0 | 187.0 | 61 |
| XS (wt %) (homopolymer) | 1.8 | 1.8 | 1.9 | 1.7 | 1.6 | 1.8 | 1.6 |
| RX 2 Conditions | | | | | | | |
| Rx 2 Temp (C.) | 70 | 70 | 70 | 70 | 70 | 70 | 70 |
| Rx 2 Propylene partial pressure (kPa) | 724 | 704 | 704 | 655 | 538 | 565 | 283 |
| Rx 2 residence time (hours) | 2 | 2.1 | 4.4 | 2 | 2.1 | 2 | 1 |
| Rx 2 $H_2/C_3$ | 0.266 | 0.288 | 0.285 | 0.023 | 0.022 | 0.017 | 0.096 |
| Rx 2 $C_2/C_3$ | 1.75 | 1.7 | 1.69 | 3 | 3 | 2.5 | 1.5 |
| MFR (dg/min) | 82 | 90 | 88 | 79 | 79 | 86 | 31 |
| Pellet Product Properties | | | | | | | |
| MFR (g/10 min) | 101 | 100 | 90 | 78 | 74 | 82 | 33 |
| Ec (% wt) | 49.2 | 50.9 | 48.9 | 44.5 | 45.2 | 43.4 | 52 |
| Fc (% wt) | 19.8 | 18.2 | 19.1 | 17.3 | 16.9 | 18.4 | 17 |
| Gardner Impact @−30° C., J | 5.5 | 2.3 | 3.7 | Na | na | na | na |
| Volatiles Content (µg/g) | 21 | 22 | 26 | 47.7 | 55.6 | 46.9 | 125 |

*= Comparative

Samples A-G are compounded with the additives listed in Table 4 using twin screw, intermeshing extruders. Samples A-F are compounded using a 25 mM W&P twin screw extruder and sample G is compounded on a W&P ZSK 280 twin screw extruder. No purging is done on these samples following the compounding.

TABLE 3

| Nucleated with 1000 ppmw NA-11 | A | B | C | D* | E* | F* | G* |
|---|---|---|---|---|---|---|---|
| ISO Flex Chord (psi) | na | na | Na | 1,526 | 1,529 | 1,362 | 1,493† |
| ISO Notched Izod @23° C. (KJ/M$^2$) | na | na | Na | 7.49 | 7.81 | 10 | 8.3† |
| ASTM 1% secant flex modulus (MPa) | 1541 | 1590 | 1575 | Na | na | na | 1539 |
| ASTM RT Izod (J/m) | 30 | 27 | 27 | Na | na | na | 76 |

*= Comparative
†= Values calculated based on a correlation to the ASTM values listed in the table

TABLE 4

| Additives (ppmw) | Examples A-C | Examples D-F |
| --- | --- | --- |
| Irganox 1010 (hindered phenolic antioxidant) | 1000 | 1000 |
| Irgafos 168 (Phosphite Antioxidant) | 1000 | 1000 |
| GMS (glycerol monostearate) | na | 6000 |
| Calcium Stearate (acid acceptor) | 600 | 600 |
| If nucleated with NA-11 | | |
| NA-11 - nucleating agent | 1000 | 1000 |

Samples A-C have a lower volatiles content than comparative Samples D-G in spite of the fact that Samples A-C each have a higher MFR than Samples D-G.

Samples A-C show that a catalyst with a substituted 1,2 phenylene dibenzoate (in combination with DCPDMS) produces a propylene impact copolymer with high melt flow and a low volatiles content. Surprisingly and unexpectedly, the present propylene impact copolymer produced is superior in volatiles content. In particular, samples A-C each have a smaller volatiles content than samples D-G.

It is specifically intended that the present invention not be limited to the embodiments and illustrations contained herein, but include modified forms of those embodiments including portions of the embodiments and combinations of elements of different embodiments as come within the scope of the following claims.

The invention claimed is:

1. A polymerization process comprising:
   contacting, under polymerization conditions, propylene with a catalyst composition comprising a substituted phenylene aromatic diester in a first polymerization reactor;
   forming an active propylene-based polymer;
   contacting, under polymerization conditions, the active propylene-based polymer with at least one olefin in a second polymerization reactor; and
   forming a propylene impact copolymer comprising a substituted phenylene aromatic diester.

2. The process of claim 1 comprising forming a propylene impact copolymer having a volatiles content less than about 30 μg/g in accordance with VW standard PV3341.

3. The process of claim 1 wherein the catalyst composition comprises aluminum, the process comprising adding an external electron donor to at least one of the polymerization reactors and maintaining an Al: EED ratio of less than 5.0.

4. The process of claim 3 comprising adding a single external electron donor.

5. The process of claim 1 comprising forming an active propylene-based polymer having a melt flow rate greater than 100 g/10 min as measured in accordance with ASTM D 1238, 2.16 kg, 230° C.

6. The process of claim 1 comprising forming a propylene impact copolymer having a melt flow rate greater than 40 g/10 min as measured in accordance with ASTM D 1238, 2.16 kg, 230° C.

7. The process of claim 1 comprising maintaining a $H_2/C_3$ mole ratio of greater than 0.1 in the second polymerization reactor.

8. The process of claim 1 comprising contacting, in the second polymerization reactor, the active propylene-based polymer with propylene and ethylene and forming a propylene impact copolymer having an Fc value from about 5 wt % to about 50 wt % and an Ec value from about 20 wt % about 90 wt %.

9. A propylene impact copolymer comprising:
   a propylene-based polymer;
   a propylene/ethylene copolymer dispersed within the propylene-based polymer; and
   a substituted phenylene aromatic diester.

10. The propylene impact copolymer of claim 9 wherein the substituted phenylene diester is present in a member selected from the group consisting of the propylene-based polymer, the propylene/ethylene copolymer, and combinations thereof.

11. The propylene impact copolymer of claim 9 comprising 3-methyl-5-tert-butyl-1,2 phenylene dibenzoate.

12. The propylene impact copolymer of claim 9 having a volatiles content less than about 30 μg/g as measured in accordance with VW standard PV3341.

13. The propylene impact copolymer of claim 9 wherein the propylene-based polymer has a melt flow rate (MFR) greater than about 100 g/10 min as measured in accordance with ASTM D 1238-01 (230° C., 2.16 kg).

14. The propylene impact copolymer of claim 9 wherein the propylene impact copolymer has a melt flow rate (MFR) greater than about 40 g/10 min as measured in accordance with ASTM D 1238-01 (230° C., 2.16 kg).

15. The propylene impact copolymer of claim 9 wherein the propylene-based polymer has a property selected from the group consisting of a xylene solubles content less than about 4%, a $T_{MF}$ greater than about 170° C., and combinations thereof.

16. The propylene impact copolymer of claim 9 wherein the propylene impact copolymer has an Fc value from about 5 wt % to about 50 wt %, an Ec value from about 20 wt % to about 90 wt %.

17. An article comprising:
   a propylene impact copolymer comprising 3-methyl-5-tert-butyl-1,2 phenylene dibenzoate.

18. The article of claim 17 having a volatiles content less than about 30 μg/g as measured in accordance with VW standard PV3341.

19. The article of claim 17 selected from the group consisting of an extruded article, an injection molded article, a rotational molded article, a blow molded article, and a thermoformed article.

20. The article of claim 17 wherein the propylene impact copolymer has a melt flow rate greater than about 40 g/10 min as measured in accordance with ASTM D 1238-01(230° C., 2.16 kg).

* * * * *